United States Patent [19]
Bullard

[11] Patent Number: 5,842,973
[45] Date of Patent: Dec. 1, 1998

[54] NASAL INTUBATION APPARATUS

[76] Inventor: James Roger Bullard, P.O. Box 14727, Augusta, Ga. 30919-0727

[21] Appl. No.: 883,793

[22] Filed: Jun. 27, 1997

Related U.S. Application Data

[63] Continuation-in-part of Ser. No. 645,442, May 13, 1996, Pat. No. 5,665,052, which is a continuation of Ser. No. 245,026, May 17, 1994, Pat. No. 5,551,946.

[60] Provisional appllication No. 60/021,873, Jul. 17, 1996.

[51] Int. Cl.$^6$ ........................................................ A61B 1/26
[52] U.S. Cl. ............................ 600/194; 600/114; 600/120
[58] Field of Search ..................................... 600/114, 120, 600/167, 188, 194, 197, 199, 187; 128/207.14

[56] References Cited

U.S. PATENT DOCUMENTS

| | | |
|---|---|---|
| 3,677,262 | 7/1972 | Zuukowski . |
| 3,776,222 | 12/1973 | Smiddy . |
| 3,802,440 | 4/1974 | Salem et al. . |
| 4,150,676 | 4/1979 | Jackson . |
| 4,449,522 | 5/1984 | Baum . |
| 4,659,328 | 4/1987 | Potter et al. . |
| 4,947,896 | 8/1990 | Bartlett . |
| 4,949,716 | 8/1990 | Chenoweth . |
| 5,058,577 | 10/1991 | Six . |
| 5,259,377 | 11/1993 | Schroeder . |
| 5,285,778 | 2/1994 | Mackin . |
| 5,329,940 | 7/1994 | Adair . |
| 5,551,946 | 9/1996 | Bullard . |
| 5,665,052 | 9/1997 | Bullard . |

OTHER PUBLICATIONS

Circon ACMI Operating and Maintenance Manual Catalog No. LAR–P Pediatric, LAR–A Adult "Bullard™ Intubating Laryngoscopes".

*Primary Examiner*—Beverly M. Flanagan
*Attorney, Agent, or Firm*—St. Onge Steward Johnston & Reens LLC

[57] ABSTRACT

A nasal intubation apparatus comprises a curved rigid body having a distal end and a proximal end joined by a curved section which approximates the curvature of the transition of the normal human nasopharynx to the oropharynx. The body has provided in it fiberoptic viewing and illumination channels. A working channel is provided to permit use of a flexible guide member to act as a guide for positioning of an endotracheal tube fitted over the intubation apparatus body. A controllable tip section at the distal end of the body is provided.

32 Claims, 4 Drawing Sheets

NASAL INTUBATION APPARATUS

This application is based on, and I claim priority rights under 35 U.S.C. §119(e) from, U.S. Provisional patent application Ser. No. 60/021,873, filed Jul. 17, 1996; the present application is also a continuation in part of my copending application Ser. No. 08/645,442, filed May 13, 1996 and entitled "Multifunctional Intubating Guide Stylet and Laryngoscope", now U.S. Pat. No. 5,665.052,which is a continuation of Ser. No. 08/245,026 filed May 17, 1994, now issued as U.S. Pat. No. 5,551,946.

1. Field of the Invention

The present invention relates to the field of medical optical devices permitting diagnosis and minimally invasive treatment and surgery, and more particularly, to an improved nasal intubation apparatus.

2. Background of the Invention

Oral laryngoscopes are used to facilitate endotracheal intubation of a patient during surgery to provide a positive air passageway for the administration of anesthesia and/or for the mechanical ventilation of the lungs of the patient. In the human anatomy, the epiglottis normally overlies the glottic opening into the larynx to prevent the passage of food into the trachea during eating; therefore, in endotracheal intubation, it is necessary to displace the epiglottis from the glottic opening to permit the endotracheal tube to be inserted into the trachea.

A laryngoscope having means for indirect illumination and visualization of the pharyngeal areas of the body is disclosed in my U.S. Pat. No. 4,086,919, the disclosure of which is hereby incorporated by reference. U.S. Pat. No. 4,086,919 discloses a laryngoscope (hereafter the "Bullard Laryngoscope") for endotracheal intubation which comprises a housing containing a working channel for containing forceps and channels containing fiber optics for lighting and viewing the internal areas of the body; and a laryngoscope blade for manipulating the epiglottis of a patient to enable viewing of a target area.

Various other laryngoscope constructions are known. Other prior art laryngoscope have consisted of a metal blade which is supportably attached to a handle and is inserted through the mouth of the patient into the pharyngeal area to displace the tongue and epiglottis and permit direct visualization of the glottic opening through the mouth opening. Such laryngoscope have been provided with a light source which is directed along the blade to illuminate the area beyond the distal end of the blade Two general types of rigid blade constructions are the straight, or so called "Miller blade", and the slightly curved, or so called "Macintosh blade". Curved laryngoscope blade constructions having light means to facilitate illumination of the areas of observation are described in U.S. Pat. Nos. 3,598,113; 3,643,654; 3,766,909; and 3,771,514. The Bullard Laryngoscope improves over these prior art laryngoscope by providing an apparatus permitting the simple and rapid visualization of a target area such as the glottis to guide the insertion of an endotracheal tube.

In some cases, an oral intubation is not desirable or practicable and a nasal intubation must be established. There are typically three available techniques for nasal intubation. One method of nasal intubation, if clinical conditions permit, is to observe the placement of the nasal endotracheal tube using an oral laryngoscope. A second method is what is referred to as the "blind" approach, manipulating the tube and/or patient's head and neck. A third, and one most frequently used at this time, is the approach using a flexible fiberoptic bronchoscope ("F.O.B.") to both guide and visually confirm the proper placement of the endotracheal tube.

The nasal intubation route is generally regarded as requiring a curved path. However, anatomically the nasal route is less curved than the oral pathway. The nasal pathway follows the superior aspect of the hard palate, the lateral aspect of the nasal septum inferiorly to the lower most turbinate in a line that is essentially straight and parallel from the external nare to the nasopharynx.

The nasopharynx transitions to the oropharynx at an almost 90° angle. In the oropharynx, the posterior pharyngeal wall passes the base of the tongue and epiglottis located anteriorly. Just past these structures, one arrives at the laryngeal aditus. The laryngeal aditus gives access to the inner-located structures of the larynx, these being the laryngeal cartilages, true and false vocal cords, and, principally, the glottis allowing access to the trachea.

The "blind" nasal intubation has certain risks associated with it. Customarily this procedure involves inserting a flexible plastic hollow endotracheal tube through a nostril, advancing it through the nasal cavity, and through the nasopharynx and the oropharynx into the trachea. However, this procedure can traumatize the nasal mucosa, causing bleeding and laceration of the mucosa. In addition, it is difficult to advance the tube around the near 90 degree transition between the nasal cavity and the oropharynx. Lastly, even if these anatomical structures have been successfully navigated, the tube must still make a final turn to enter the trachea. It is to be appreciated that the "blind" approach can take multiple attempts at insertion before the endotracheal tube is successfully established. In critical cases, time is of the essence, and the time involved in establishing the endotracheal tube can decrease the prospects for a successful medical procedure.

Nasal intubation using an oral laryngoscope makes the final step of the procedure, insertion of the endotracheal tube into the trachea, more rapid and easier by allowing direct vision of the location of the end of the endotracheal tube, so that it can be manipulated into the proper position. However, the oral laryngoscope does not assist in the negotiation of the nasal cavity and the nasal cavity/oropharynx transition because it is positioned below these structures.

Nasal intubation using a flexible F.O.B. theoretically provides the most reliable approach, as in this method the endoscope is fitted over the flexible F.O.B., and the F.O.B. provides direct vision of the insertion path of the nasal endotracheal tube. However, this method requires significant training to become proficient with the technique. It is estimated that 25 to 50 practice intubations on a mannequin followed by 50 to 100 intubations on normal patients is required before a physician should attempts what is termed "difficult airway management".

In addition, a F.O.B. is expensive, very delicate, and requires the utmost care to prevent damage. Repair is costly and takes the instrument out of use. One of the main problems in the use of the fiberoptic bronchoscope is a reflection of one of its benefits—that is, its flexibility. It is often difficult to control the F.O.B. as it is advanced through the patient airways to the vocal cords. Although the F.O.B. has a controllable tip permitting "up" or "down" movements, it is still a difficult instrument to handle effectively.

Typically the F.O.B. is passed through the most patent nostril (if used orally, a special airway of considerable dimensions must be employed to protect and guide the tip) until the operator observes the pharyngeal structures, such as the base of the tongue and/or the epiglottis. In most anesthetized patients the pharyngeal structures "in-fall" precluding clear views of the larynx. Therefore, the F.O.B. must be maintained in the mid-line and advanced beyond these screening structures until laryngeal structures are visualized. Typically, the epiglottis must be elevated to allow accurate visualization. This may require the use of a separate instrument, such as an oral laryngoscope, to manipulate the epiglottis. After the tip of the fiberoptic bronchoscope has passed below the epiglottis and has entered the laryngeal outlet, the vocal cords are visualized and the tip is advanced below the cords. The endotracheal tube is then passed off of the F.O.B. through the vocal cords. When the endotracheal tube inner diameter more closely approximates the outer diameter of the F.O.B., easier passage through the cords is achieved. The greater the disparity between these two measurements the more likely the endotracheal tube will "hang-up" on the laryngeal structures, such as the arytenoids, requiring manipulative techniques and increasing time required.

SUMMARY OF THE INVENTION

It is an object of the invention to provide a nasal intubation apparatus and method to quickly and accurately introduce and position a nasally introduced endotracheal tube.

These objects, and other objects as disclosed in this application, are achieved by a nasal intubation apparatus and method as described below.

An intubating apparatus in accordance with the invention comprises a rigid, narrow, curved body which is sized to receive an endotracheal tube thereon and to be fitted into human nasal and pharyngeal passageways. The body has a proximal end and a distal end, and a curved section joining the proximal and distal ends. The joining section has a curvature approximating the curvature of the transition of the normal human nasopharynx to the oropharynx. Preferably this is an angle in the range of 80–100 degrees, and most preferably this is a 90 degree angle. The body has provided in it optical viewing and illumination channels containing a flexible optical image transmitting medium extending from the distal end to the proximal end of the intubating apparatus. Preferably, a working channel is provided that extends the length of the body. The working channel has an inner diameter adapted to permit a flexible guide member having a distal end to be passed therethrough, such that, upon passage of a flexible guide member through the working channel, the flexible guide member will be manipulated to position the guide member at a desired position in a patient's anatomy with direct vision by the optical illumination and viewing channels, such that an endotracheal tube, when mounted to the body, may be advanced along the body onto the guide member to be positioned in the patient at the desired position in the patient's anatomy. Preferably, the intubating apparatus has a controllable tip section provided at its distal end. The controllable tip section is pivotable in a single direction, to about a 45 degree deflection, from a home position which is aligned with the distal end of the apparatus to a pivoted position, and the optical viewing and illumination channels are pivoted with the controllable tip section.

A method of intubating a patient in accordance using the above described apparatus comprises the steps of: introducing the intubation apparatus in a supine patient's nasal passageway; advancing the distal end of the intubation apparatus to traverse the superior aspect of the hard palate generally parallel to the hard palate; rotating the intubation apparatus until the proximal end thereof is generally vertical while advancing the distal end of the intubation apparatus past the patient's tongue and epiglottis until the patient's glottis is viewed by said optical viewing channel; advancing the endotracheal tube on the intubation apparatus to cause the distal end of the endotracheal tube to pass through the patient's glottis and into the patient's trachea; and removing the intubation apparatus from the patient, leaving the endotracheal tube positioned with its distal end in the patient's trachea. In a preferred embodiment, the method further comprises passing a flexible guide member through the working channel provided in the body, until a distal end of the flexible guide member is located adjacent to the distal end of the body; viewing the patient's glottis using the optical viewing channel; advancing the flexible guide member between the patient's vocal cords into the patient's trachea; advancing the endotracheal tube along the flexible guide member and the intubation apparatus to position the endotracheal tube for ventilation of the patient; and removing the guide member and intubation apparatus from the patient.

Other objects, aspects and features of the present invention in addition to those mentioned above will be pointed out in detail or will be understood from the following detailed description provided in conjunction with the accompanying drawings.

BRIEF DESCRIPTION OF THE DRAWINGS

The foregoing aspects and other features of the invention are explained in the following description, taken in connection with the accompanying drawings, wherein.

DETAILED DESCRIPTION OF THE INVENTION

Figure 1:
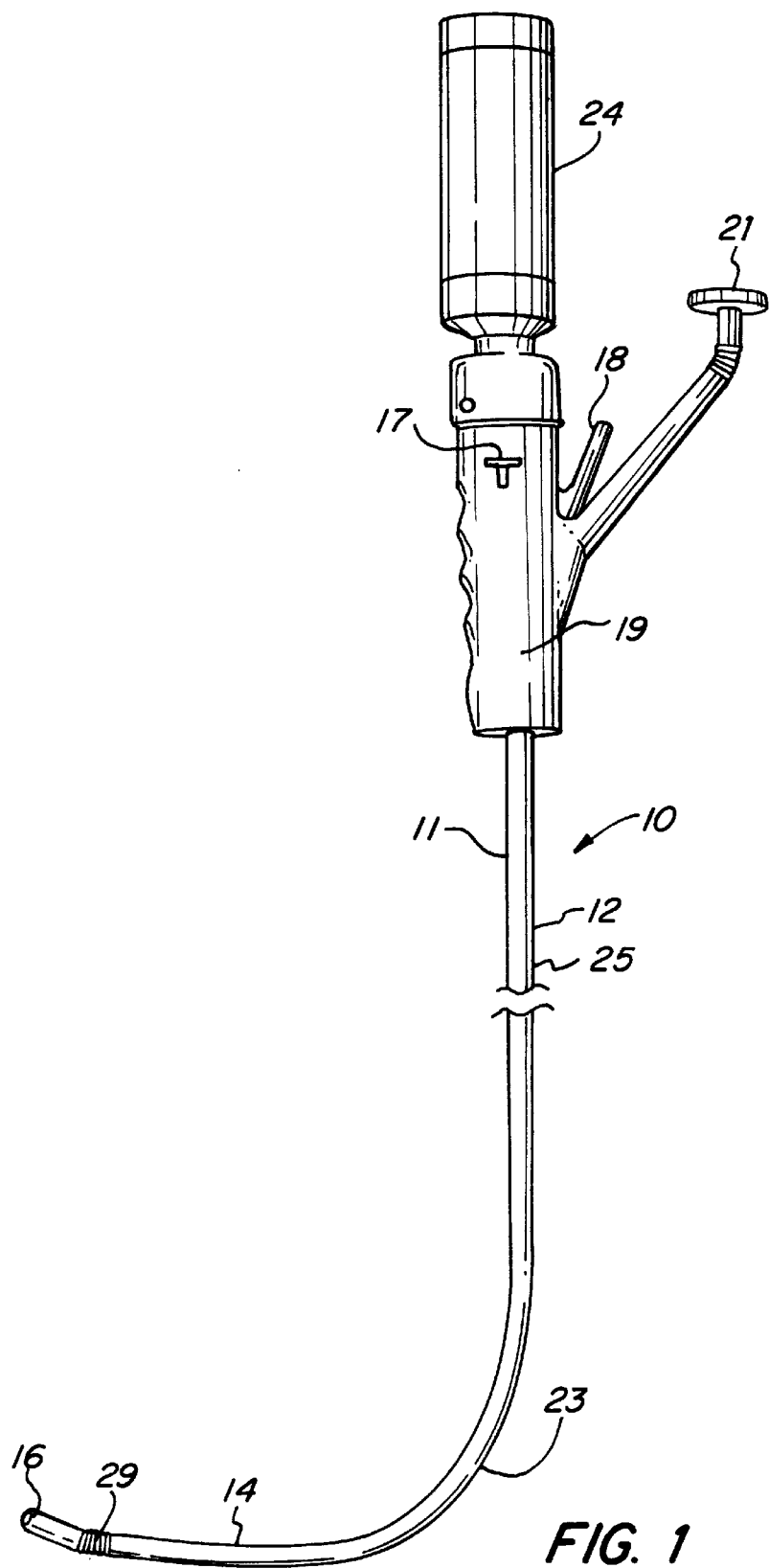
FIG. 1 is a perspective view of a nasal intubation apparatus in accordance with the invention.
Figure 2:
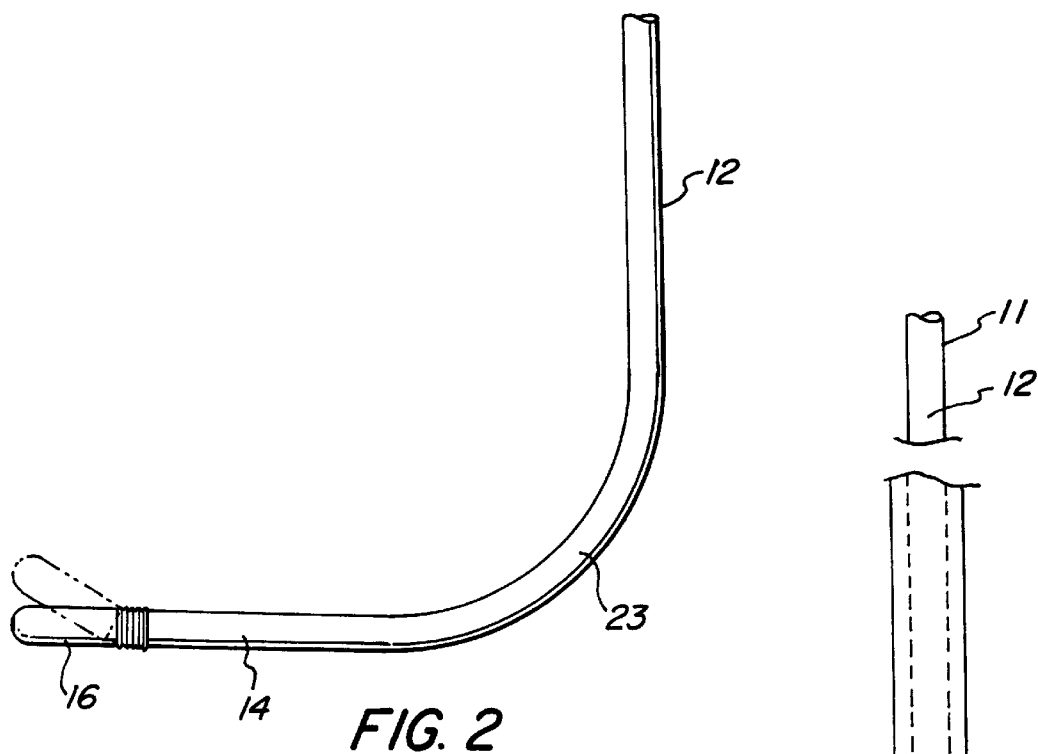
FIG. 2 is a detail view of the controlled targeting distal end section of the nasal intubation apparatus of FIG. 1.
Figure 3:
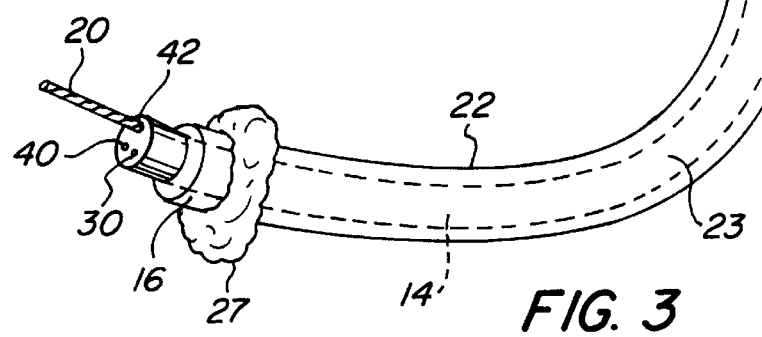
FIG. 3 is a detail view of the distal end section of the nasal intubation apparatus of FIG. 1 showing the use of the apparatus with an endotracheal tube.

Referring now to FIGS. 1–6, the nasal intubation apparatus of this disclosure comprises an L-shaped rigid intubation apparatus 10 suitable for introduction into the above described nasal pathway. Intubation apparatus 10 comprises a body 11 preferably constructed from stainless steel or another medically acceptable, rigid, durable material. Intubation apparatus 10 has a proximal (upper) end 12 and a distal (lower) end 14. Proximal end 12 is preferably approximately 30 cm in length. Distal end 14 is preferably approximately 11 cm in length.

Intubation apparatus 10 is for use in an adult patient, and the section 23 joining the proximal end 12 to the distal end 14 is curved to generally conform with the curvature of the transition of the normal human nasopharynx to the oropharynx, at about a ninety degree angle, preferably within a range of about 80–100 degrees. In a pediatric laryngoscope, the section 23 will be curved through about a ninety degree angle though with a much smaller radius of curvature than the adult laryngoscope.

Intubation apparatus 10, being sized to fit into the nare and nasal passageways, is quite narrow, and has a maximum cross-sectional distance or diameter between the limits of its outer wall 25 of between about 2 mm to about 10 mm, most preferably about 2 mm to about 6 mm. Preferably intubation apparatus 10 is circular in cross-section.

Figure 4:
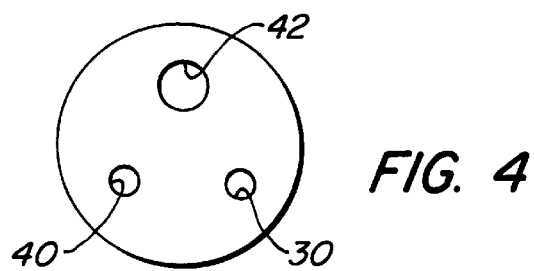
FIG. 4 is a detail end view of the distal end of the nasal intubation apparatus of FIG. 1.

Intubation apparatus 10 preferably has a plurality of channels provided for flexible fiberoptic bundles for viewing and illumination of the patient's anatomy as shown in FIG. 4. The channels extend from the proximal end 12 to the distal end 14 of the intubation apparatus 10. Optical viewing channel 30 is provided with a flexible optical image transmitting medium, which is preferably a bundle of optic fibers which extend from the proximal end 12 to the distal end 14 of the intubation apparatus 10. The optical image transmitting medium in the optical channel 30 permits optical images to betransmitted through the optical channel 30. A viewing lens 32 on the distal end of the optical channel 38 collects optical images for transmission through the optical channel 30. The viewing fiberoptic bundles will be provided with a focusing eyepiece lens 21 at their proximal end. Preferably the eyepiece shaft is flexible.

Intubation apparatus 10 is preferably adapted so that a video camera may be operably coupled to the proximal end 12 of the intubation apparatus 10 at the proximal end of the optical channel 30 to receive and transmit the optical images from the optical channel 30 to a television monitor (not shown) and to a video recording apparatus such as a video cassette recorder (not shown).

Light channel 40 is provided with the light transmitting medium that permits light to be transmitted through the light channel 40. This permits the illumination of the field where treatment, diagnosis or operations are desired. The light transmitting medium is preferably a plurality of optic fibers with another suitable lens at the distal end thereof as necessary. The light transmitting medium is connected at its proximal end to a light source of a sufficiently high intensity to permit visualization of the field. The light source may for example comprise a halogen bulb located in battery handle 24, but may be an independent light source attached to a light post.

Preferably, a working channel 42 will also be included in the device, also as shown in FIG. 4. The working channel will be provided with a Luer lock port at its proximal end 18. The working channel 42 can receive a flexible guide member 20, such as a catheter, or be used for suction, insufflation of oxygen, or injection of local anesthetics such as with a hollow catheter.

In a preferred embodiment, the distal most 3 cm of the distal end would possess a targeting feature; that is, the controllable tip section 16 could be manipulated to pivot from its normal home position aligned with the distal end 12 through approximately 45° in accordance with my U.S. Pat. No. 5,318,008, and my application serial no. Ser. No. 08/287,711, filed Aug. 9, 1994, entitled "Controlled Targeting Laryngoscope," the disclosures of which are hereby incorporated by reference. This movement would be in one direction only, that is from horizontal or 0° to + (plus) 45°; NOT through a 90° arc (from − (minus) 45° to + (plus) 45°). The reason for this deflection is to overcome severe degrees of the condition commonly known as "anterior larynx". The worst cases being seen in conditions characterized by glossoptosis. A thumb control 17 for the control targeting mechanism will be preferably provided at the hand-grip 19 for the nasal intubation apparatus 10. The thumb control 17 operates on and causes a cable to push the controllable tip section 16 to a deflected position within its range of movement. A spring is provided to bias the thumb control 17 to its upward position thereby keeping the controllable tip section 16 in its normal, home position, until pressure is applied to the thumb control. A rubber sleeve 29 such as a corrugated rubber sleeve fits around the body at the connection to the controllable tip section 16 to seal the instrument control mechanisms from exposure to bodily fluids.

The use of the nasal intubation apparatus 10 is as follows.

Figure 5:
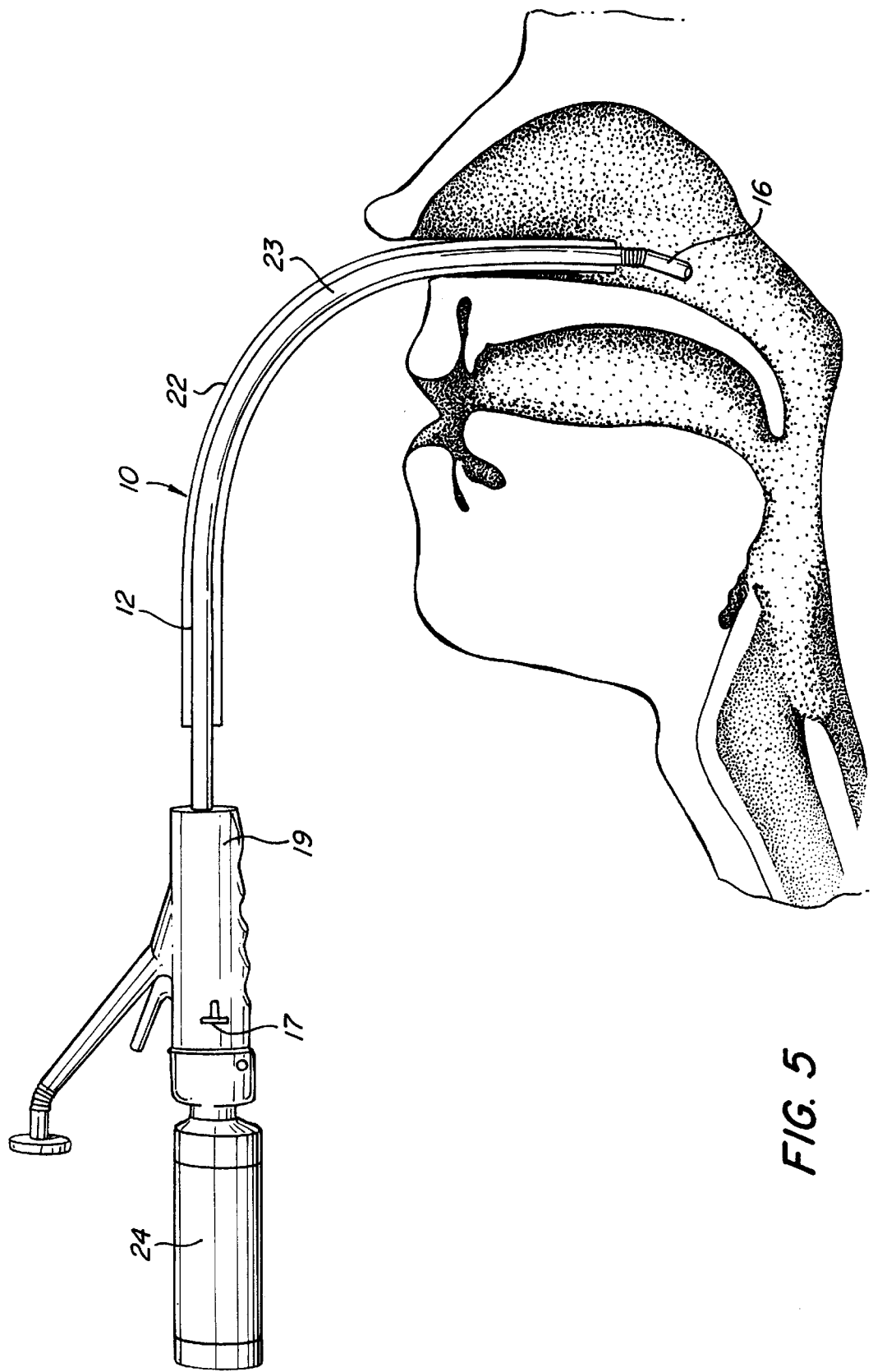
FIG. 5 is a side elevation view with partial cutaway view showing an embodiment of a nasal intubation apparatus as it is being introduced into a patient.
Figure 6:
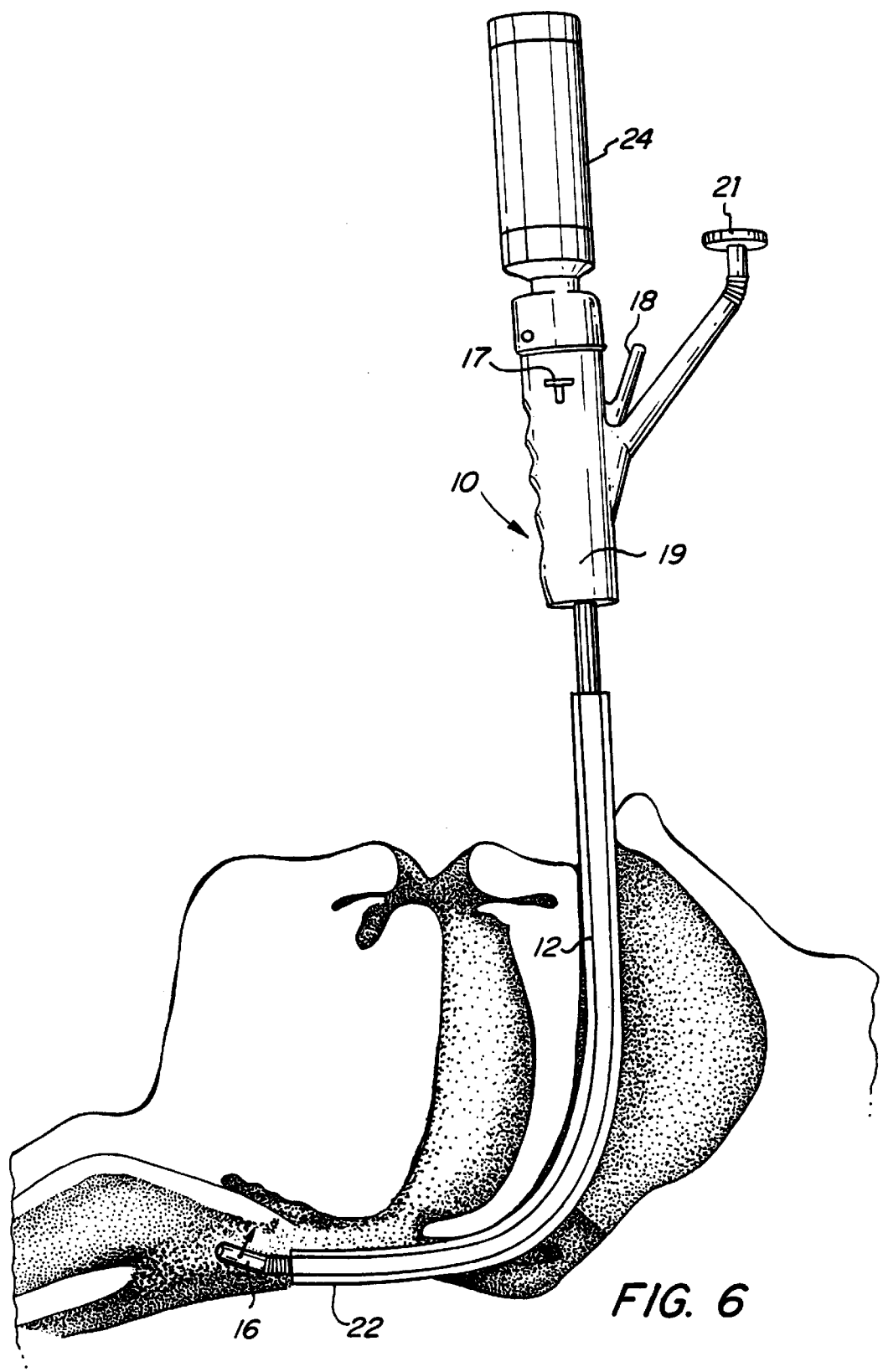
FIG. 6 is a side elevation view with partial cutaway view showing an embodiment of a nasal intubation apparatus established in a patient.

After preparation of the patient, either awake or under general anesthesia in a supine position, the proper size endotracheal tube 22 is loaded over the shaft of the nasal intubation apparatus 10. The distal end 14 of the nasal intubation apparatus 10 is introduced into the selected nare with the distal end 14 manipulated to traverse the superior aspect of the hard palate generally parallel to the hard palate, as shown in FIG. 5. The nasal intubation apparatus 10 is then gently rotated through 90° until the proximal end 12 is vertical and the pharyngeal structures are visualized, as shown in FIG. 6. Most likely, the objects visualized will be the base of the tongue or epiglottis. The intubating apparatus 10 is then advanced past these structures in an atraumatic fashion, and, if necessary, the distal tip 16 elevated to move the epiglottis for visualization of the glottis and largngeal aditus. The midline position is more easily maintained with nasal placement.

In the preferred embodiment, a flexible guide member 20 is advanced through the working channel 42 and through the glottis for guiding the endotracheal tube 22. The flexible guide member 20 may be passed through the working channel 42 prior to the introduction of the intubation apparatus 10 into the patient, or it may be inserted inside the working channel 42 after the intubation apparatus 10 is established or partially introduced into the patient.

The endotracheal tube 22 is then advanced in a sliding motion off the distal shaft, through the glottis and into the trachea. Proper positioning of the inflatable endotracheal tube cuff 27 below the cords would be visualized through the intubation apparatus 10. If desired, the flexible guide member 20 may be withdrawn and a proper sized bronchoscope could be passed through the working channel 42 or via the previously placed endotracheal tube for absolute confirmation of position.

The flexible guide member 20 that is passed through the working channel 42 may comprise a medical optical apparatus such as a bronchoscope, or it may be a flexible hollow catheter, or even, in some instances, a solid flexible rod. If flexible guide member 20 is a catheter, it may be used to deliver an anesthetic to laryngeal and subglottic areas. In alternative embodiments, the catheter may serve as a conduit for high frequency jet ventilation of the patient's lungs; or as a suctioning catheter; or a bronchial blocker, i.e. an inflatable collar might be affixed to the end of the catheter and inflated when the catheter is positioned in the right or left main stem bronchus, thus blocking off one lung from the other.

In one preferred embodiment, the flexible guide member 20 comprises a flexible directable medical optical apparatus such as a bronchoscope. In this case the medical optical apparatus is advanced to at least the location of the patient's mid-trachea during the step of advancing the guide member 20 prior to establishing the endotracheal tube 22. The medical optical apparatus may also be advanced into the patient's lung cavities to permit inspection of the lungs. This permits rapid and accurate placement of a bronchoscope, which can be a crucial life-saving element when there is an urgent need to remove a blocking foreign body in the patient's trachea.

In another preferred embodiment of the invention, the flexible guide member 20 may comprise a flexible hollow catheter. A liquid surface anesthetic may be injected through such a catheter to spray and anesthetize laryngeal and subglottic area of the patient prior to establishing the endotracheal tube. The catheter may be used for high frequency jet ventilation to the patient's lungs. The catheter may also be used to provide suction to a proximal end of the catheter to suction secretions from the patient. The invention thus provides a flexible method of locating such a catheter and to perform the above procedures without the additional step of manually locating such a catheter, because it is already located when the patient is intubated. The catheter may be left in place in the endotracheal tube and sealed with a luer lock, so that it is available for use as needed.

The intubation apparatus 10 is removed while firmly fixing the endotracheal tube 22 in place in exactly the same reverse manner as inserted. The endotracheal tube 22 may then be connected to a source of oxygen to ventilate the patient or it may be connected to a source of anesthetic or therapeutic gases.

The new nasal intubation apparatus 10 would greatly facilitate the nasal endotracheal intubation of the majority of patients now requiring the more difficult and complicated techniques in use. The device would be rugged, easily cleaned, very portable (utilizing the battery handle with built in light source 24), with a rapid learning curve, and easily maintained skills.

It is to be appreciated that the intubation apparatus of the present invention could also be used in oral intubation procedures if desired, although it is intended for use in nasal intubation procedures.

The method provides the benefits of visual certainty as to where the guide member 20 and endotracheal tube 22 are being located; it reduces trauma caused by the repetitive efforts to establish an endotracheal tube 22 which were often required with prior art devices and methods. The present invention permits effective use of the intubation apparatus 10 in a variety of physical structures, by permitting the physician greater control of the placement of the endotracheal tube 22.

The present invention provides an important and timely contribution to the art of medical devices, by providing a nasal intubation apparatus that has better operational flexibility than any device known in the art.

It is to be appreciated that the foregoing is illustrative and not limiting of the invention, and that various changes and modifications to the preferred embodiments described above will be apparent to those skilled in the art. Such changes and modifications can be made without departing from the spirit and scope of the present invention, and it is therefore intended that such changes and modifications be covered by the following claims.

I claim:

1. A nasal intubating apparatus, comprising:
    a rigid curved body, said body having an outer wall surface sized to receive an endotracheal tube thereon and to be fitted into human nasal and pharyngeal passageways, said body having a proximal end and a distal end, and a curved section joining said proximal and distal ends having a curvature approximating the curvature of the transition of the normal human nasopharynx to the oropharynx;
    an optical viewing channel containing a flexible optical image transmitting medium extending from said distal end of said apparatus to said proximal end of said apparatus; and
    an optical illumination channel containing a flexible optical image transmitting medium extending from said distal end of said apparatus to said proximal end of said apparatus.

2. An intubation apparatus in accordance with claim 1, wherein said curved section joins said proximal and distal ends of said intubation apparatus at an angle of about 80 to about 100 degrees.

3. An intubation apparatus in accordance with claim 2, wherein said curved section joins said proximal and distal ends of said intubation apparatus at an angle of about 90 degrees.

4. An intubating apparatus in accordance with claim 1, further comprising a working channel extending from said distal end to a port provided at said proximal end of said apparatus, said working channel having an inner diameter adapted to permit a flexible guide member having a distal end to be passed therethrough, such that, upon passage of a flexible guide member through said working channel, the flexible guide member will be manipulated to position the guide member at a desired position in a patient's anatomy with direct vision by said optical illumination channel and said optical viewing channel, such that an endotracheal tube, when mounted to said body, may be advanced along the body onto the guide member to be positioned in the patient at the desired position in the patient's anatomy.

5. An intubating apparatus in accordance with claim 4, wherein a flexible guide member is provided inside of said working channel.

6. An intubating apparatus in accordance with claim 5, wherein said flexible guide member comprises a medical optical apparatus.

7. An intubating apparatus in accordance with claim 5, wherein said flexible guide member comprises a flexible hollow catheter.

8. An intubating apparatus in accordance with claim 7, wherein said flexible hollow catheter comprises a catheter selected from the group consisting of an anesthetic delivery catheter; a high frequency jet ventilation catheter; a suctioning catheter; and a bronchial blocking catheter.

9. An intubating apparatus in accordance with claim 1, further comprising an endotracheal tube fitted onto said body.

10. An intubating apparatus in accordance with claim 1, further comprising a controllable tip section provided at said distal end of said apparatus, said controllable tip section being pivotable in a single direction from a home position which is aligned with said distal end of said apparatus to a pivoted position, and in which said optical viewing channel and said optical illumination channel are pivoted with said controllable tip section.

11. An intubating apparatus in accordance with claim 10, in which said controllable tip section is pivotable to a position which is about 45 degrees from said home position.

12. An intubation apparatus in accordance with claim 1 wherein said outer wall surface of said body has a maximum cross-sectional distance of between about 2 mm to about 10 mm.

13. An intubation apparatus in accordance with claim 12 wherein said outer wall surface of said body has a maximum cross-sectional distance of between about 2 mm to about 6 mm.

14. An intubating apparatus, comprising:
    a rigid curved body, said body having an outer wall surface sized to receive an endotracheal tube thereon and to be fitted into human nasal and pharyngeal passageways, said body having a proximal end and a distal end, and a curved section joining said proximal and distal ends having a curvature approximating the curvature of the transition of the normal human nasopharynx to the oropharynx;

an optical viewing channel containing a flexible optical image transmitting medium extending from said distal end of said apparatus to said proximal end of said apparatus;

an optical illumination channel containing a flexible optical image transmitting medium extending from said distal end of said apparatus to said proximal end of said apparatus; and a working channel extending from said distal end to a port provided at said proximal end of said apparatus, said working channel having an inner diameter adapted to permit a flexible guide member having a distal end to be passed therethrough, such that, upon passage of a flexible guide member through said working channel, the flexible guide member will be manipulated to position the guide member at a desired position in a patient's anatomy with direct vision by said optical illumination channel and said optical viewing channel, such that an endotracheal tube, when mounted to said body, may be advanced along the body onto the guide member to be positioned in the patient at the desired position in the patient's anatomy.

15. An intubation apparatus in accordance with claim 14, wherein said curved section joins said proximal and distal ends of said intubation apparatus at an angle of about 80 to about 100 degrees.

16. An intubation apparatus in accordance with claim 15, wherein said curved section joins said proximal and distal ends of said intubation apparatus at an angle of about 90 degrees.

17. An intubating apparatus in accordance with claim 14, wherein a flexible guide member is provided inside of said working channel.

18. An intubating apparatus in accordance with claim 17, wherein said flexible guide member comprises a medical optical apparatus.

19. An intubating apparatus in accordance with claim 17, wherein said flexible guide member comprises a flexible hollow catheter.

20. An intubating apparatus in accordance with claim 19, wherein said flexible hollow catheter comprises a catheter selected from the group consisting of an anesthetic delivery catheter; a high frequency jet ventilation catheter; a suctioning catheter; and a bronchial blocking catheter.

21. An intubating apparatus in accordance with claim 14, further comprising an endotracheal tube fitted onto said body.

22. An intubating apparatus in accordance with claim 14, further comprising a controllable tip section provided at said distal end of said apparatus, said controllable tip section being pivotable in a single direction from a home position which is aligned with said distal end of said apparatus to a pivoted position, and in which said optical viewing channel and said optical illumination channel are pivoted with said controllable tip section.

23. An intubating apparatus in accordance with claim 22, in which said controllable tip section is pivotable to a position which is about 45 degrees from said home position.

24. An intubating apparatus, comprising:
a rigid curved body, said body having an outer wall surface sized to receive an endotracheal tube thereon and to be fitted into human nasal and pharyngeal passageways, said body having a proximal end and a distal end, and a curved section joining said proximal and distal ends having a curvature approximating the curvature of the transition of the normal human nasopharynx to the oropharynx;

an optical viewing channel containing a flexible optical image transmitting medium extending from said distal end of said apparatus to said proximal end of said apparatus;

an optical illumination channel containing a flexible optical image transmitting medium extending from said distal end of said apparatus to said proximal end of said apparatus;

a working channel extending from said distal end to a port provided at said proximal end of said apparatus, said working channel having an inner diameter adapted to permit a flexible guide member having a distal end to be passed therethrough, such that, upon passage of a flexible guide member through said working channel, the flexible guide member will be manipulated to position the guide member at a desired position in a patient's anatomy with direct vision by said optical illumination channel and said optical viewing channel, such that an endotracheal tube, when mounted to said body, may be advanced along the body onto the guide member to be positioned in the patient at the desired position in the patient's anatomy; and a controllable tip section provided at said distal end of said apparatus, said controllable tip section being pivotable in a single direction from a home position which is aligned with said distal end of said apparatus to a pivoted position, and in which said optical viewing channel and said optical illumination channel are pivoted with said controllable tip section.

25. An intubation apparatus in accordance with claim 24, wherein said curved section joins said proximal and distal ends of said intubation apparatus at an angle of about 80 to about 100 degrees.

26. An intubating apparatus in accordance with claim 25, wherein a flexible guide member is provided inside of said working channel.

27. An intubating apparatus in accordance with claim 26, further comprising an endotracheal tube fitted onto said body.

28. An intubating apparatus in accordance with claim 10, in which said controllable tip section is pivotable to a position which is about 45 degrees from said home position.

29. An intubation apparatus in accordance with claim 24 wherein said outer wall surface of said body has a maximum cross-sectional distance of between about 2 mm to about 10 mm.

30. An intubation apparatus in accordance with claim 29 wherein said outer wall surface of said body has a maximum cross-sectional distance of between about 2 mm to about 6 mm.

31. A method of nasally intubating a patient, comprising the steps of:
introducing an intubation apparatus in a supine patient's nasal passageway, said intubation apparatus comprising
a rigid curved body, said body having an outer wall surface sized to receive an endotracheal tube thereon and to be fitted into human nasal and pharyngeal passageways, said body having a proximal end and a distal end, and a curved section joining said proximal and distal ends having a curvature approximating the curvature of the transition of the normal human nasopharynx to the oropharynx; an optical viewing channel containing a flexible optical image transmitting medium extending from said distal end of said apparatus to said proximal end of said apparatus; an optical illumination channel containing a flexible optical image transmitting medium extending from said distal end of said apparatus to said proximal end of said apparatus; and an endotracheal tube having a distal end and a proximal end mounted onto said body;

advancing said distal end of said intubation apparatus to traverse the superior aspect of the hard palate generally parallel to the hard palate;

rotating said intubation apparatus until said proximal end of said intubation apparatus is generally vertical while advancing said distal end of said intubation apparatus past the patient's tongue and epiglottis until the patient's glottis is viewed by said optical viewing channel;

advancing said endotracheal tube on said intubation apparatus to cause said distal end of said endotracheal tube to pass through the patient's glottis and into the patient's trachea; and removing said intubation apparatus from said patient, leaving said endotracheal tube positioned with its distal end positioned in the patient's trachea.

32. A method of intubating a patient in accordance with claim 31, further comprising:

passing a flexible guide member through a working channel provided in said body, until a distal end of said flexible guide member is located adjacent to the distal end of said body;

viewing the patient's glottis using the optical viewing channel;

advancing the flexible guide member between the patient's vocal cords into the patient's trachea;

advancing the endotracheal tube along said flexible guide member and said intubation apparatus to position the endotracheal tube for ventilation of the patient; and removing the guide member and intubation apparatus from the patient.

* * * * *